(12) United States Patent
Brumsted et al.

(10) Patent No.: US 8,779,150 B2
(45) Date of Patent: Jul. 15, 2014

(54) PROCESSES FOR THE MANUFACTURE OF PROPANE-1-SULFONIC ACID {3-[5-(4-CHLORO-PHENYL)-1 H-PYRROLO[2,3-B]PYRIDINE-3-CARBONYL]-2,4-DIFLUORO-PHENYL}-AMIDE

(75) Inventors: Corey James Brumsted, Corvallis, OR (US); Hendrik Moorlag, Basel (CH); Roumen Nikolaev Radinov, West Caldwell, NJ (US); Yi Ren, Shanghai (CN); Pius Waldmeier, Wegenstetten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 181 days.

(21) Appl. No.: 13/183,694

(22) Filed: Jul. 15, 2011

(65) Prior Publication Data
US 2012/0022258 A1 Jan. 26, 2012

(30) Foreign Application Priority Data

Jul. 21, 2010 (EP) .................................... 10170266

(51) Int. Cl.
C07D 513/04 (2006.01)
C07D 213/73 (2006.01)

(52) U.S. Cl.
USPC .......................................... 546/311; 546/114

(58) Field of Classification Search
USPC ................................................ 546/311, 114
See application file for complete search history.

(56) References Cited

U.S. PATENT DOCUMENTS

| | | | |
|---|---|---|---|
| 6,476,045 B1 | 11/2002 | Dinnell et al. | |
| 7,361,763 B2 * | 4/2008 | Arnold et al. | 546/113 |
| 7,504,509 B2 | 3/2009 | Ibrahim et al. | |
| 8,329,724 B2 | 12/2012 | Hildbrand et al. | |
| 8,530,661 B2 | 9/2013 | Hildbrand et al. | |
| 2006/0183758 A1* | 8/2006 | Beard et al. | 514/260.1 |
| 2013/0005761 A1 | 1/2013 | Hildbrand et al. | |

FOREIGN PATENT DOCUMENTS

| | | |
|---|---|---|
| WO | 98/58935 | 12/1998 |
| WO | 2006/015123 | 2/2006 |
| WO | 2007/002325 | 1/2007 |
| WO | 2007/002433 | 1/2007 |
| WO | 2009/016460 | 2/2009 |

OTHER PUBLICATIONS

Whelligan "Two-Step Synthesis of Aza- and Diazaindoles from Chloroamino-N-heterocycles Using Ethoxyvinylborolane" J. Org. Chem. 2010, 75, 11-15, published online Dec. 1, 2009.*
Zhao, S-B et al., Organometallics (XP002630313), 29(4):998-1003 (Jan. 1, 2009).
Kumar, V. et al., Journal of Organic Chemistry (XP000578238), 57(25):6995-6998 (Dec. 4, 1992).
(International Search Report for PCT/EP2011/062207 Nov. 29, 2011).
Pillard, C. et al., Synthesis (XP002630167), 13:2049-2054 (May 2008).
(International Search Report for PCT/EP2010/061079 Feb. 17, 2011).
Satoh et al., "Synthesis":373 ( 1987).
Written Opinion of the International Searching Authority mailed on Dec. 17, 2012 for PCT Patent Application No. PCT/EP2011/062207 filed on Jul. 18, 2011, ten pages.

* cited by examiner

*Primary Examiner* — David K O Dell
(74) *Attorney, Agent, or Firm* — Morrison & Foerster LLP

(57) ABSTRACT

According to the present invention there are provided novel processes for the manufacture of the compound of formula 1

(1)

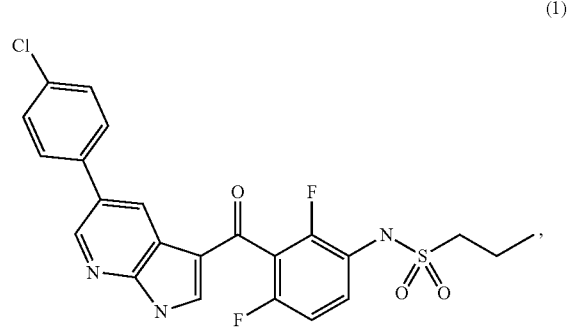

as well as intermediates and novel synthesis routes for key intermediates used in those processes.

6 Claims, No Drawings

PROCESSES FOR THE MANUFACTURE OF PROPANE-1-SULFONIC ACID {3-[5-(4-CHLORO-PHENYL)-1 H-PYRROLO[2,3-B]PYRIDINE-3-CARBONYL]-2,4-DIFLUORO-PHENYL}-AMIDE

PRIORITY TO RELATED APPLICATION(S)

This application claims the benefit of European Patent Application No. 10170266.0, filed Jul. 21, 2010, which is hereby incorporated by reference in its entirety.

FIELD OF THE INVENTION

The present invention is related to alternative synthesis routes to obtain the compound Propane-1-sulfonic acid {3-[5-(4-chloro-phenyl)-1H-pyrrolo[2,3-b]pyridine-3-carbonyl]-2,4-difluoro-phenyl}-amide (formula 1).

Formula 1

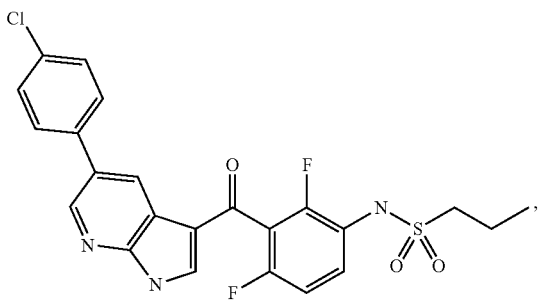

The synthesis of the compound of formula 1 has been described before in WO 2007002433 and WO 2007002325.

The present invention discloses alternative reactions to obtain compound 1. The reactions and processes disclosed herein use few reaction steps, and lead to good overall yield of compound 1, inter alia due to few separation steps and work-up procedures. Moreover, the processes disclosed herein can be carried out with relatively small amounts of starting material and may therefore be safer for use in large scale production, interesting from a cost perspective and environmentally friendly. In addition, the present invention provides novel synthesis methods to obtain key intermediates used in the manufacture of the compound of formula 1. One group of said key intermediates involves 5-substituted-7-azaindoles. Another group of key intermediates involves pinacol vinyl-boronates.

SUMMARY OF THE INVENTION

The present invention relates in part to a process for the manufacture of the compound of formula 1, (1)

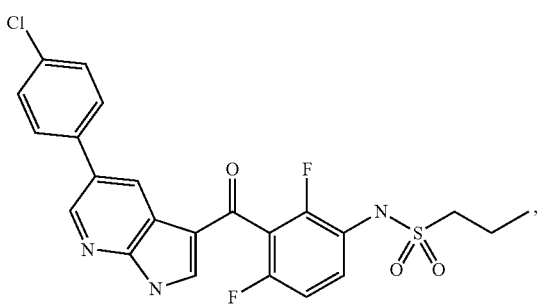

comprising at least one Suzuki-Miyaura reaction followed by a Friedel-Crafts acylation.

The present invention also relates to a process for the manufacture of a compound of formula A, (A)

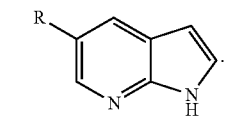

The present invention further relates to a process for the manufacture of the compound of formula D (D)

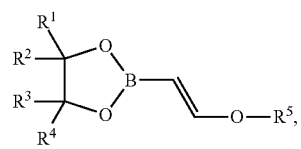

wherein $R^1$, $R^2$, $R^3$ and $R^4$ are all methyl, or together with the carbon atoms to which they are attached form a phenyl ring; and $R^5$ is —(C1-C6)alkyl or benzyl.

In addition, the present invention relates to a compound of formula E (E)

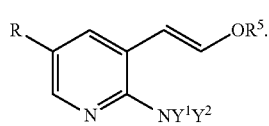

wherein

R is phenyl, which is unsubstituted or once or several times substituted by halogen, or —Br;

$R^5$ is —(C1-C6)alkyl or benzyl; and $Y^1$ and $Y^2$ are each independently selected from the group consisting of benzyl, trifluoroacetyl, acetyl, and hydrogen.

The present invention further relates to a compound of formula F (F)

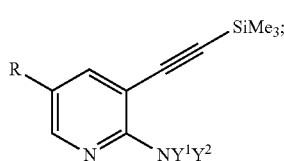

wherein

R is phenyl, which is unsubstituted or once or several times substituted by halogen, or —Br; and $Y^1$ and $Y^2$ are each independently selected from the group consisting of benzyl, trifluoroacetyl, acetyl, and hydrogen.

DETAILED DESCRIPTION OF THE INVENTION

In one embodiment the present invention provides a process for the manufacture of the compound of formula 1,

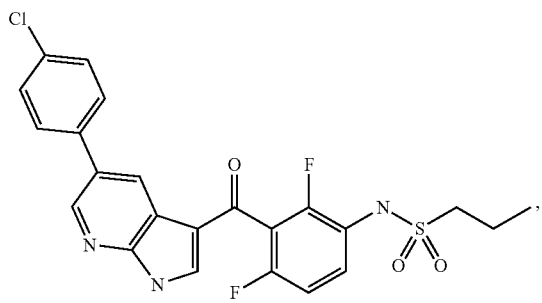
(1)

comprising at least one Suzuki-Miyaura reaction followed by a Friedel-Crafts acylation.

In another embodiment the present invention provides a process for the manufacture of the compound of formula 1, comprising two Suzuki-Miyaura reactions followed by a Friedel-Crafts acylation.

In another embodiment the present invention provides a process for the manufacture of the compound of formula 1, comprising one Suzuki-Miyaura reaction followed by a Sonogashira reaction, further followed by a Friedel-Crafts acylation.

In a preferred embodiment according to the present invention, the first Suzuki-Miyaura reaction in each of the processes as described above is followed by a halogenation reaction, in particular a reaction step for introducing a halogen atom, preferably iodo or bromo, into the corresponding intermediate.

More particularly, there is provided a process for the manufacture of the compound of formula 1, wherein a) the compound of formula 2

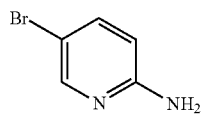
(2)

is reacted in the presence of a palladium catalyst, a base and the compound of formula 3 ($1^{st}$ Suzuki-Miyaura reaction)

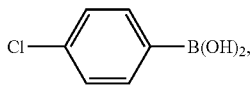
(3)

to give the compound of formula 4

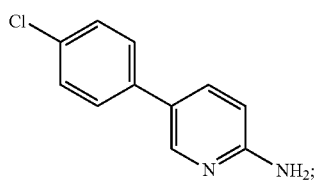
(4)

b) said compound of formula 4 is further reacted in the presence of a halogenation reagent to give a compound of formula 5

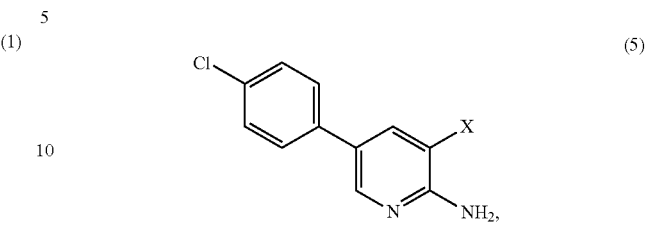
(5)

wherein X is I (5a) or Br (5b); and said compound of formula 5 is further reacted in the presence of either c-1) a compound of formula (D) ($2^{nd}$ Miyaura reaction); or c-2) a compound of formula 7 (Sonogashira reaction)

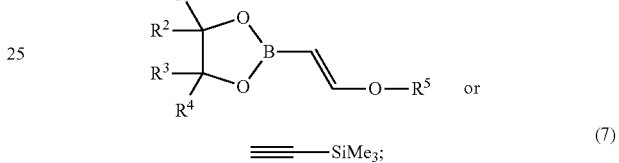
(D)

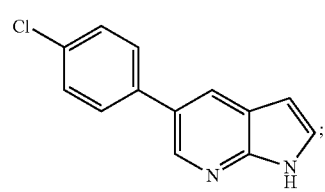
(7)

to give the compound of formula 8

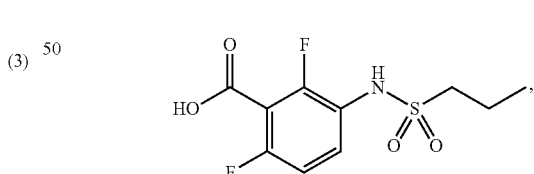
(8)

and d) said compound of formula 8 is subsequently reacted in the presence of the compound of formula 9 and under the conditions of a Friedel-Crafts Acylation (9)

to give the compound of formula 1, wherein $R^1$, $R^2$, $R^3$ and $R^4$ are all methyl, or together with the carbon atoms to which they are attached form a phenyl ring; and $R^5$ is —(C1-C6)alkyl or benzyl.

In another preferred embodiment there is provided the above described process wherein $R^1$ to $R^4$ are all methyl; and $R^5$ is ethyl.

In still another embodiment according to the present invention there is provided the above described process a) to d) for the manufacture of the compound of formula 1, wherein steps a) and b) are as described above; and c-1) said compound of formula 5 according to step b) is further reacted in the presence of a palladium catalyst and a base, which can both be the same or different as under step a), and the compound of formula D

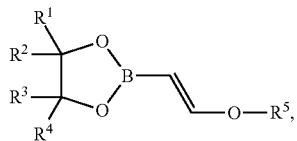
(D)

followed by treatment with an acid to give the compound of formula 8

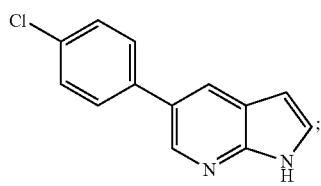
(8)

and d) said compound of formula 8 is further reacted with the compound of formula 9

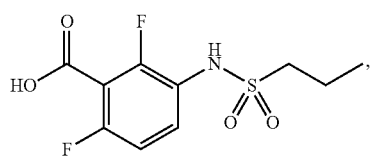
(9)

In the presence of (COCl)₂ and AlCl₃, to give the compound of formula 1, and $R^1$ to $R^5$ are as defined above.

In still another preferred embodiment according to the present invention there is provided the process for the manufacture of the compound of formula 1 according to steps a) to d) above, wherein a) the compound of formula 2

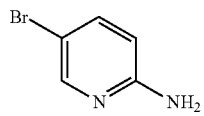
(2)

is reacted in the presence of PdCl₂(dppf)CH₂Cl₂, Pd(OAc)₂, Na₂CO₃ and the compound of formula 3

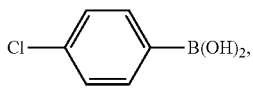
(3)

to give the compound of formula 4

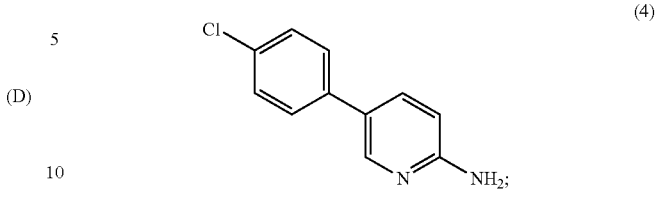
(4)

b) said compound of formula 4 is further reacted in the presence of N-iodosuccinimide (NIS) and CF₃COOH, or N-bromosuccinimide (NBS) to give a compound of formula 5

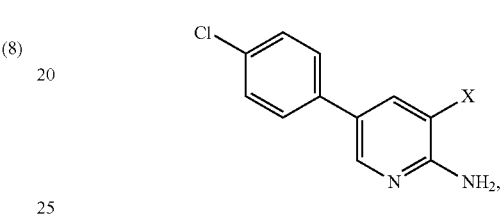
(5)

wherein X is —I (5a) or —Br (5b);

c-1) said compound of formula 5 is further reacted in the presence of PdCl₂(dppf)CH₂Cl₂, LiOH and the compound of formula 6,

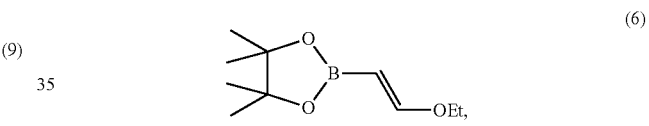
(6)

and subsequently treated with HCl to give the compound of formula 8

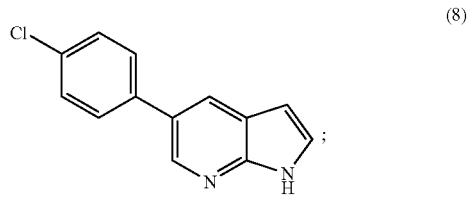 [SMILES: Clc1ccc(-c2cnc3[nH]ccc3c2)cc1]
(8)

and d) said compound of formula 8 is further reacted with the compound of formula 9

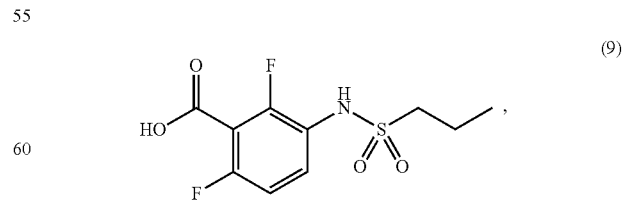
(9)

In the presence of (COCl)₂ and AlCl₃, to give the compound of formula 1.

In an especially preferred embodiment according to the present invention, the reaction step b) prior to the reaction step c-1) as mentioned above is carried out in the presence of NBS to give the compound of formula 5, wherein X is bromo (5b).

In yet another embodiment according to the present invention there is provided a process for the manufacture of the compound of formula 1, wherein reaction steps a) and b) are as described herein before; and c-2) the compound of formula 5 from reaction step b) is further reacted in the presence of a palladium catalyst and a base, which may both be the same or different as in step a), CuI, tetramethylguanidine (TMG) and the compound of formula 7,

(7)

followed by the reaction with a strong base, to give the compound of formula 8

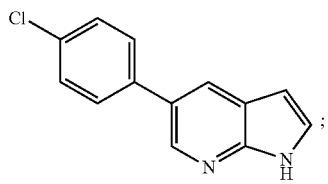
(8)

and d) said compound of formula 8 is further reacted with the compound of formula 9

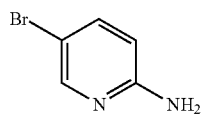
(9)

In the presence of (COCl)$_2$ and AlCl$_3$, to give the compound of formula 1.

In a still preferred embodiment according to the present invention, there is provided the process for the manufacture of the compound of formula 1 according to steps a) to d) above, wherein a) the compound of formula 2

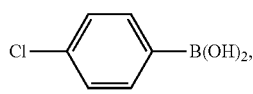
(2)

is reacted in the presence of PdCl$_2$(dppf)CH$_2$Cl$_2$, Pd(OAc)$_2$, Na$_2$CO$_3$ and the compound of formula 3

(3)

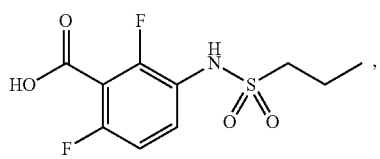

to give the compound of formula 4

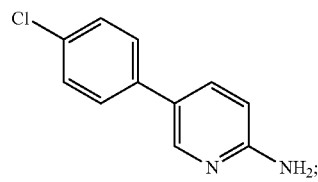
(4)

b) said compound of formula 4 is further reacted in the presence of N-iodosuccinimide (NIS) and CF$_3$COOH, or N-bromosuccinimide (NBS) to give a compound of formula 5

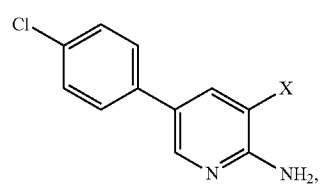
(5)

wherein X is —I (5a) or —Br (5b);

c-2) said compound of formula 5 is further reacted in the presence of Pd(PPh$_3$)$_2$Cl$_2$, CuI, tetramethylguanidine (TMG) and the compound of formula 7,

(7)

followed by the reaction with KOtBu in NMP, to give the compound of formula 8

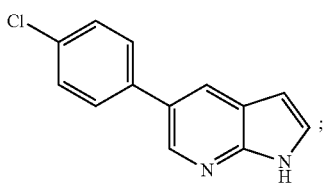
(8)

and d) said compound of formula 8 is further reacted with the compound of formula 9

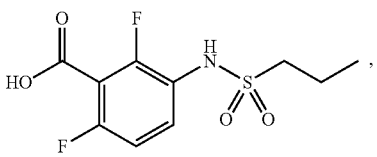
(9)

In the presence of (COCl)$_2$ and AlCl$_3$, to give the compound of formula 1.

In still another preferred embodiment there is provided the process as described above, wherein the reaction step b) prior to the reaction step c-2) is carried out in the presence of NBS to give the compound of formula 5, wherein X is bromo (5b).

General Synthesis Route

The reaction partners and conditions of the above-mentioned Suzuki-Miyaura-, Sonogashira- and Friedel Crafts reactions are generally known to the person of skill in the art of synthetic organic chemistry and are inter alia described or referred to in common textbooks of Organic Chemistry. If not explicitly otherwise stated, the above described preferred reaction conditions to obtain the compound of formula 1 can be summarized, but not limited, according to the following general reaction scheme 1. The key reaction step according to the present invention, namely the reactions from compound 5 to 8, can be accomplished either via the reaction with a compound D, preferably the compound 6 (Suzuki-Miyaura Route) or via the reaction with compound 7 (Sonogashira Route):

in the presence of an acid. Suitable acids are well known to the person of skill in the art and encompass organic and inorganic or mineral acids. Preferred acids according to the present invention are HCl, $H_2SO_4$, $HNO_3$, $CF_3COOH$ and the like; with HCl being especially preferred.

According to the present invention, the preferred reaction partner in the Sonogashira reaction is ethynyltrimethylsilane (7). The reaction is preferably carried out in the presence of $Pd(PPh_3)_2Cl_2$ and CuI in toluene. Strong bases in N-methyl-2-pyrrolidone (NMP) subsequently used in the reaction to obtain the compound of formula (8) are bases with a higher strength than those used in the Suzuki-Miyaura reactions

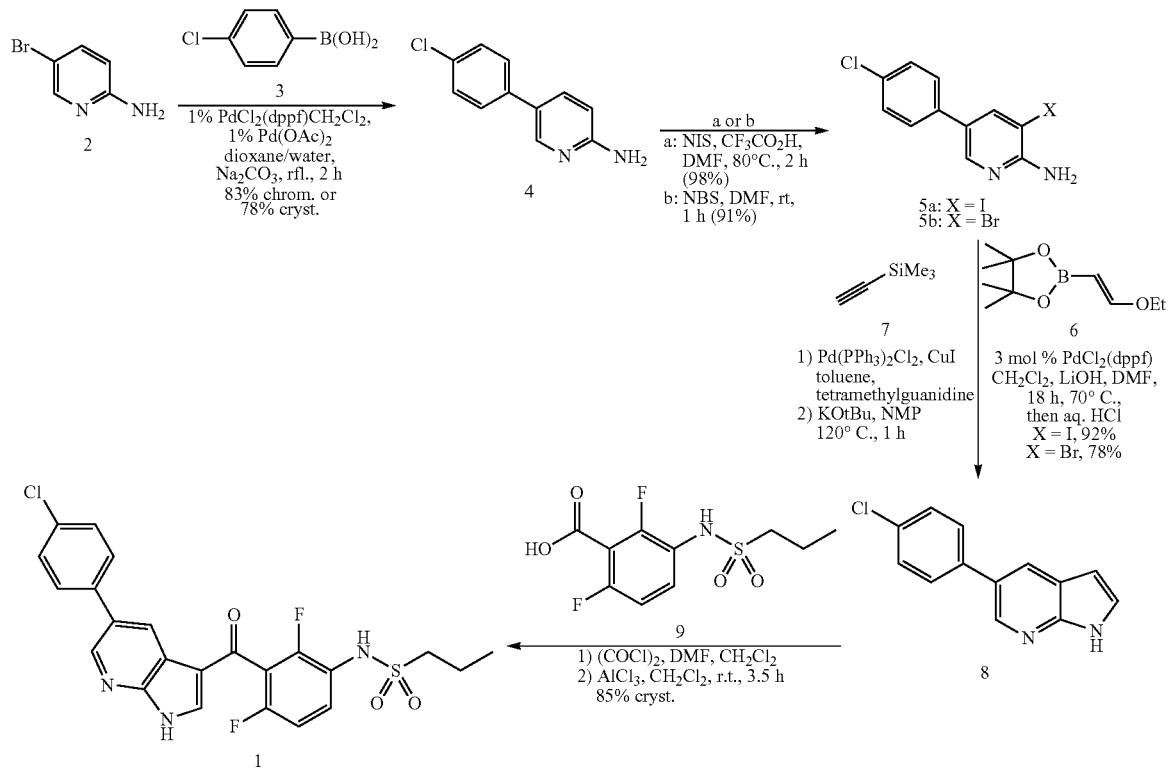

scheme 1

In accordance with the present invention, the reaction partner of the first Suzuki-Miyaura reaction is 4-chlorophenylboronic acid (3). The reaction partner of the second Suzuki-Miyaura reaction is a vinyl ether boronate of formula (D), such as catechol vinylboronate or pinacol vinylboronate (1-ethoxyethene-2-boronic acid pinacol ester, 6), with the pinacol vinylboronate being especially preferred. If not explicitly otherwise stated the compounds (D) or (6) are present as mixtures of their E/Z isomers.

The reaction is carried out in the presence of palladium (Pd) catalysts, more preferably, $PdCl_2(dppf)CH_2Cl_2$, $Pd(OAc)_2$ and the like. In addition, both Suzuki-Miyaura reactions take place under basic conditions (pH-values above 7) in organic solvents or mixtures of organic solvents with water. Preferred bases according to the present invention are organic bases or alkali metal bases, more particularly $N(CH_2CH_3)_3$, $Na_2CO_3$, LiOH and the like. Preferred organic solvents are toluene, dimethylformamide (DMF) or mixtures of dioxane and water.

Subsequent to the second Suzuki-Miyaura reaction the compound of formula (8) is obtained by cyclization-reaction together with the palladium catalysts as described before. Such strong bases are preferably alkali metal alcoholates and the like. Especially preferred according to the present invention is KOtBu used in N-methyl-2-pyrrolidone (NMP).

The Suzuki-Miyaura- and Sonogashira reactions are preferably carried out in a temperature range between 70 and 120° C., or under reflux of the solvent or solvent mixture used.

The final Friedel-Crafts reaction, also named Friedel-Crafts acylation, preferably takes place in the presence of $(COCl)_2$ and $AlCl_3$ in DMF and $CH_2Cl_2$ at room temperature (rt).

The term "room temperature" (rt) as used herein means the ambient temperature of the place where the reaction is carried out without any additional heating or cooling. According to the present invention, room temperature is preferably between 18 and 26° C., more preferably 20 to 24° C.

The term —(C1-C6)alkyl as used herein means a linear or branched, saturated hydrocarbon containing from one to six carbon-atoms, preferably from 2 to 4 carbon-atoms. The most preferred —(C1-C6)alkyl group according to the present invention is ethyl.

The term "halogenation reaction" as mentioned above is a reaction of the product of the first Suzuki-Miyaura reaction with a "halogenating reagent" selected from either N-iodosuccinimide (NIS) to introduce one iodo-atom or others (e.g. I₂); or N-bromosuccinimide (NBS) to introduce one bromo-atom in said product of the first Suzuki-Miyaura reaction. The reaction with NIS is preferably carried out in the presence of trifluoroacetic acid (TFA) and DMF. The reaction with NBS is preferably carried out in DMF.

Intermediates

I) 5-substituted-7-azaindoles

One of the key features in the synthesis route towards the formula 1 according to the present invention is the new and improved method to obtain the compound of formula 8. Due to these improvements, the above described synthesis routes provide for the first time a process for the manufacture of the compound of formula 1 which is faster, cheaper and safer than the previously described processes.

Based on this, a further embodiment of the present invention is to provide a process for the manufacture of a compound of formula A,

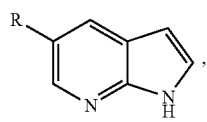
(A)

said process being characterized in that
a) a compound of formula B

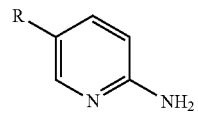
(B)

is reacted in the presence of a halogenation reagent, optionally followed by the introduction of amino-protecting groups, to give a compound of formula C

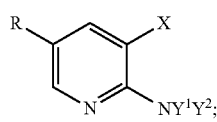
(C)

b) said compound of formula C is further reacted in the presence of a palladium catalyst, a base and a compound of the formula D or 7

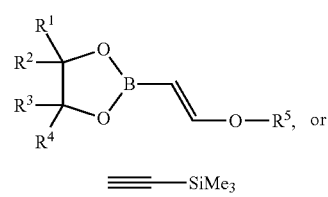
(D)

(7)

to give the compound of formula E or F, respectively

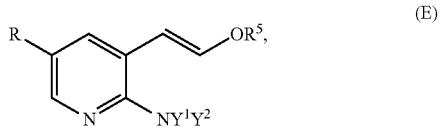
(E)

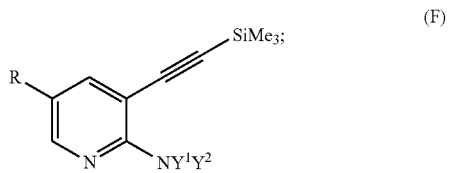
(F)

and c-1) the compound of formula E is further treated with an acid; or c-2) the compound of formula F is further treated with a strong base; to give a compound of formula A; wherein R is phenyl, which is unsubstituted or once or several times substituted by halogen, or —Br;

$R^1$, $R^2$, $R^3$ and $R^4$ are all methyl, or together with the carbon atoms to which they are attached form a phenyl ring;

$R^5$ is —(C1-C6)alkyl or benzyl;

X is —Br or —I; and $Y^1$ and $Y^2$ are each independently selected from the group consisting of benzyl, trifluoroacetyl, acetyl, and hydrogen.

The compounds of formula E and F as defined above are novel and form another embodiment of the present invention.

If not explicitly otherwise stated, the compounds of formula (D) and (E) are present as mixtures of their E/Z isomers.

The term "halogenation reagent" as used herein means N-bromosuccinimide (NBS), N-iodosuccinimide (NIS) or sodiumperiodate in combination with iodine ($I_2/NaIO_4$). For the iodination of a compound of formula B, the use of NIS in the presence of trifluoroacetic acid (TFA) is especially preferred.

The term —(C1-C6)alkyl as used herein means a linear or branched, saturated hydrocarbon containing from one to six carbon-atoms, preferably from 2 to 4 carbon-atoms. The most preferred —(C1-C6)alkyl group according to the present invention is ethyl.

The term "amino-protecting groups" as used herein means any protecting group known to the person of skill in the art of organic chemistry to protect an amino group against reactions. Preferred amino protecting groups according to the present invention are benzyl, trifluoroacetyl and acetyl.

Preferred palladium catalysts and bases as used in the process to obtain the compounds of formula A are the same as described above in connection with the reactions according to scheme 1. In particular, the reaction step b) which leads to a compound of formula E as described above is preferably carried out in the presence of $PdCl_2(dppf)CH_2Cl_2$ as Palladium catalyst, and LiOH as base. The reaction step b) which leads to a compound of formula F as described above is preferably carried out in the presence of $Pd(PPh_3)_2Cl_2$, CuI and tetramethylguanidine (TMG).

The term "strong bases" means bases with a higher strength than those used in the Suzuki-Miyaura reactions together with the palladium catalysts as described above. Preferably the term "strong bases" means alkali metal alcoholates and the like. An especially preferred strong base according to the present invention is KOtBu, which is preferably used in N-methyl-2-pyrrolidone (NMP).

The term "acid" as used herein means organic- and inorganic or mineral acids. Preferred acids according to the present invention are HCl, H$_2$SO$_4$, HNO$_3$, CF$_3$COOH and the like; with HCl being especially preferred.

In a preferred embodiment of the present invention there is provided a process for the manufacture of a compound of formula A as described above,

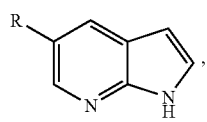
(A)

said process being characterized in that
a) a compound of formula B

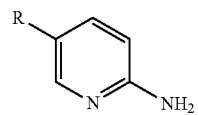
(B)

is reacted in the presence of N-bromosuccinimide (NBS) or N-iodosuccinimide (NIS) or sodiumperiodate in combination with iodine (I$_2$/NaIO$_4$), optionally followed by the introduction of amino-protecting groups, to give a compound of formula C

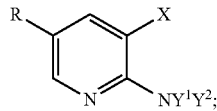
(C)

b) said compound of formula C is further reacted in the presence of PdCl$_2$(dppf)CH$_2$Cl$_2$, LiOH and a compound of the formula D

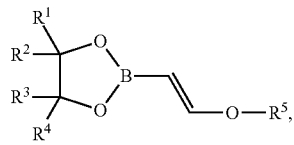
(D)

to give the compound of formula E

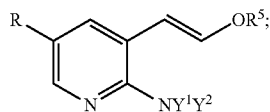
(E)

and
c-1) the compound of formula E is further treated with HCl, to give a compound of formula A; wherein
R is phenyl, which is unsubstituted or once or several times substituted by halogen, or —Br;
R$^1$, R$^2$, R$^3$ and R$^4$ are all methyl, or together with the carbon atoms to which they are attached form a phenyl ring;
R$^5$ is —(C1-C6)alkyl or benzyl;
X is —Br or —I; and
Y$^1$ and Y$^2$ are each independently selected from the group consisting of benzyl, trifluoroacetyl, acetyl, and hydrogen.

In a preferred embodiment according to the present invention there is provided the process to obtain the compound of formula A, via the compound of formula E and reaction step c-1), as described above, wherein R is —Br, and all remaining substituents are as defined above.

In another preferred embodiment according to the present invention there is provided the process to obtain the compound of formula A, via the compound of formula E and reaction step c-1), as described above, wherein R is —Br;
R$^1$ to R$^4$ are all methyl;
R$^5$ is ethyl;
X is —I; and
Y$^1$ and Y$^2$ are both hydrogen.

In another preferred embodiment according to the present invention there is provided the process to obtain the compound of formula A, via the compound of formula E and reaction step c-1), as described above, wherein R is 4-Cl-phenyl, and all remaining substituents are as defined above.

In another preferred embodiment according to the present invention there is provided the process to obtain the compound of formula A, via the compound of formula E and reaction step c-1), as described above, wherein R is 4-Cl-phenyl;
R$^1$ to R$^4$ are all methyl;
R$^5$ is ethyl;
X is —Br; and
Y$^1$ and Y$^2$ are both hydrogen.

In a further embodiment of the present invention there is provided the process for the manufacture of a compound of formula A, via the compound of formula F and reaction step c-2) as described above,

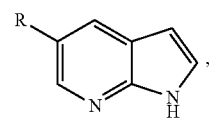
(A)

said process being characterized in that
a) a compound of formula B

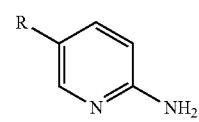
(B)

is reacted in the presence of N-bromosuccinimide (NBS) or N-iodosuccinimide (NIS) or sodiumperiodate in combination with iodine (I$_2$/NaIO$_4$), optionally followed by the introduction of amino-protecting groups, to give a compound of formula C

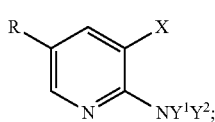

(C)

b) said compound of formula C is further reacted in the presence of Pd(PPh$_3$)$_2$Cl$_2$, CuI, tetramethylguanidine and the compound of the formula 7

(7)

to give a compound of formula F

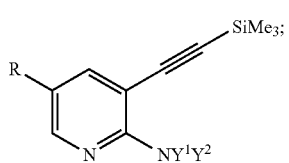

(F)

and c-2) said compound of formula F is further reacted in the presence of KOtBu to give a compound of formula A; wherein R is phenyl, which is unsubstituted or once or several times substituted by halogen, or —Br;

X is —Br or —I; and

Y$^1$ and Y$^2$ are independently selected from the group consisting of benzyl, trifluoroacetyl, acetyl, and hydrogen.

In a preferred embodiment according to the present invention, there is provided the process for the manufacture of the compounds of formula (A) via the compounds of formula (F) as described above, wherein the reaction step a) is carried out in the presence of N-iodosuccinimide (NIS) and trifluoracetic acid;

the reaction step b) is carried out in the presence of Pd(PPh$_3$)$_2$Cl$_2$, CuI, tetramethylguanidine and the compound of formula 7 in toluene;

the reaction step c-2) is carried out in the presence of KOtBu in N-methyl-2-pyrrolidon; and R is —Br;

X is —I; and

Y$^1$ and Y$^2$ are both hydrogen.

II) Pinacol Vinylboronates

According to the present invention, the above described improved synthesis of the compounds of formula A, and subsequently also of the compound of formula 1, is in particular based on the use of vinylboronates in the corresponding Suzuki-Miyaura reactions which lead to the compounds of formula A, in particular the 5—Br-7-azaindole and the 5-(4-Cl-phenyl)-7-azaindole. The use of vinylboronates and their preparation is generally known in the art.

Catechol vinylether boronate (the compound of formula D, wherein R$^1$ to R$^4$ together with the carbon-atoms to which they are attached form a phenyl ring) can be prepared according to the procedure described in Satoh, M.; Miyaura, N,; Suzuki, A.; *Synthesis* 1987, 373 and according to the following reaction scheme 2:

Scheme 2

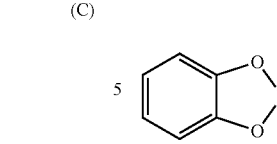

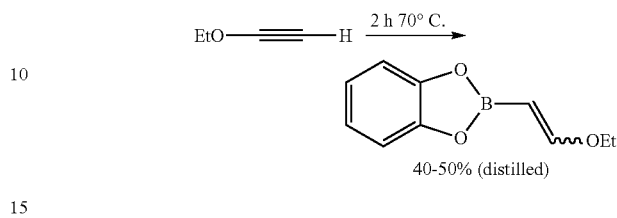

40-50% (distilled)

Pinacol vinylether boronate (the compound of formula D, wherein R$^1$ to R$^4$ are all methyl) can be prepared according to the reaction scheme 3 below.

Scheme 3

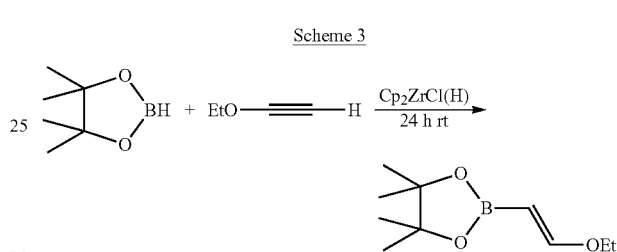

However, both synthesis routes use highly flammable ethoxyacetylene, which leads to tremendous safety concerns when used on an industrial scale.

Vinylether boronates have also been prepared using dehydrogenative borylation of alkenes. This reaction consists of a catalytic hydroboration of an alkene with a monohydrido borane, followed by the elimination of hydrogen. Rhodium, titanium and ruthenium catalysts are often used in this type of reaction. A main issue with these catalysts is that many are also efficient hydrogenation catalysts and therefore competing hydrogenation and hydroboration can occur under the reaction conditions.

There remains a need to find catalysts able to perform the dehydrogenative borylation without competing hydroboration or hydrogenation of the vinylboronate and to overcome the above described safety issues.

It has now surprisingly been found that with certain rhodium-, ruthenium- or palladium catalysts out of a list of commonly used catalysts the desired pinacol vinylether boronate was formed almost exclusively. Only small amounts (ca. 3%) of the hydroboration product could be detected.

Consequently, in another embodiment of the present invention, there is provided a process for the manufacture of the compounds of formula D (D)

wherein the compound of formula G

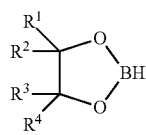

is reacted with a compound of formula H

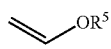

in the presence of a palladium, rhodium or ruthenium -catalyst to give a compound of formula D, wherein $R^1$, $R^2$, $R^3$ and $R^4$ are all methyl, or together with the carbon atoms to which they are attached form a phenyl ring; and $R^5$ is —(C1-C6)alkyl or benzyl.

In a preferred embodiment there is provided the above described process for the manufacture of the compounds of formula D, wherein $R^1$, $R^2$, $R^3$ and $R^4$ are all methyl; and $R^5$ is ethyl.

In another preferred embodiment the above described process for the manufacture of the compounds of formula D is carried out in the presence of $Pd(OAc)_2$, $Pd_2(dba)_3$, $Pd(NO_3)_2$, Pd/C (5%), $PdCl_2$, $Rh(OAc)_2$ or $RuCl_3$.

In another preferred embodiment the above described process for the manufacture of the compounds of formula D is carried out in the presence of 0.05 to 0.5 mol % $Pd(OAc)_2$ at room temperature.

The term "room temperature" (rt) as used herein means the ambient temperature of the place where the reaction is carried out without any additional heating or cooling. According to the present invention, room temperature is preferably between 18 and 26° C., more preferably 20 to 24° C.

The invention is now illustrated by the following accompanying, not limiting examples.

EXAMPLES

Example 1

2-amino-5-(4-chlorophenyl)-pyridine (4, first Suzuki-Miyaura reaction)

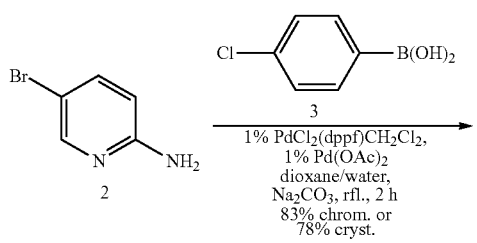

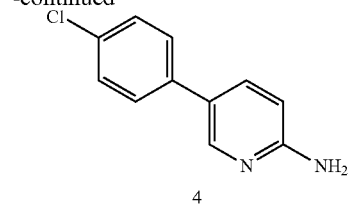

2-Amino-5-bromopyridine (2) was reacted with 4-chlorophenylboronic acid (3) in dioxane/water in the presence of 2.2 equivalents of $Na_2CO_3$ and 1 mol % $Pd(OAc)_2$ plus 1 mol % $PdCl_2(dppf).CH_2Cl_2$ at 90° C. for 1.5 h. After cooling to room temperature the product (4) was precipitated as the HCl salt by adding HCl (25%, 6 equiv) followed by removal of dioxane under vacuum. The salt was filtered, digested in diethylether, filtered and then converted to the free amine by treatment with aqueous NaOH. After filtration, the product was isolated in 78% yield. Alternatively, the product has been isolated by chromatography in 83% yield. MS (Turbo Spray): 207 (52%), 205 (M+H⁺, 100%), 170 (9%).

Example 2

Halogenation of 2-amino-5-(4-chlorophenyl)-pyridine (4)

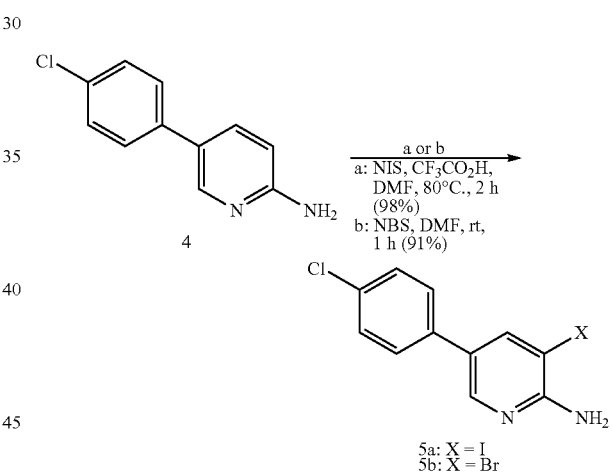

2-Amino-5-(4-chlorophenyl)-pyridine (4) was converted to the aminopyridine iodide (5a) and the aminopyridine bromide (5b). Iodination of (4) using iodine and $AgSO_4$ gave only 75% conversion after 3 days at room temperature. Better results were obtained with NIS/TFA. The pyridine bromide could be prepared using NBS.

a) Iodination of (4)

To a solution of (4) and trifluoroacetic acid (1.2 equiv) in DMF was added N-iodosuccinimide (NIS, 1.1 equiv) in DMF. After stirring for 2.5 h at 80° C., the reaction was complete. After aqueous workup, the product 5a was isolated in 98% yield. MS (Turbo Spray): 331 (100%), 205 (42%), 122 (19%).

b) Bromination of (4)

To a solution of (4) in DMF was added N-bromosuccinimide and the resulting reaction solution was stirred at room temperature for 1 h. After adding the solution to water, the product precipitated and then was filtered. Minor impurities were removed by digesting the product in hexanes. The aminopyridine bromide (5b) was isolated in a yield of 91%. MS (GC-Split): 284 (100%), 282 (77%, M), 168 (34%), 151 (14%), 140 (18%), 113 (10%).

Example 3

5-(4-Cl-phenyl)azaindole (8, via second Suzuki-Miyaura reaction)

I. Pinacol Vinylboronate Coupling

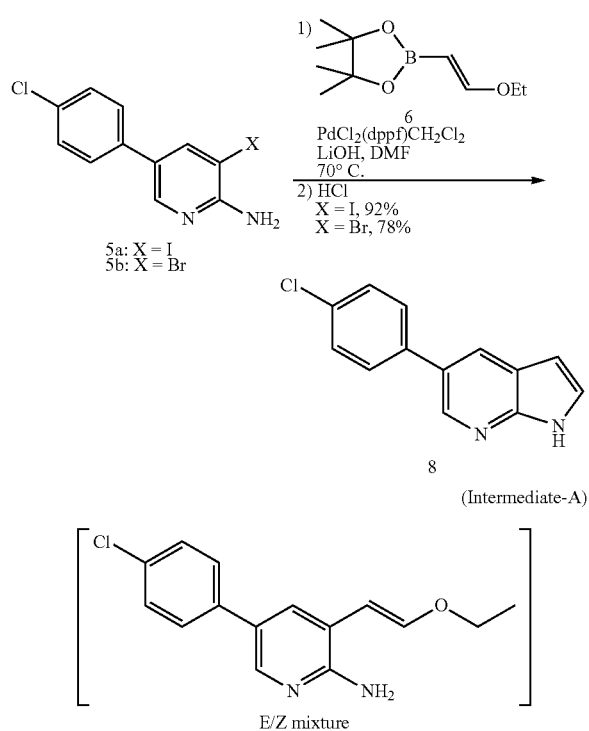

I-a) Cyclization of the Iodide (5a):

To a mixture of iodide (5a) and pinacol vinylboronate (6, 1.3 equiv) in DMF was added LiOH (3 equiv) followed by PdCl$_2$(dppf).CH$_2$Cl$_2$ (3 mol %) under an inert atmosphere (Ar). The reaction mixture was heated to 70° C. and stirred for 18 h. HPLC analysis indicated complete conversion to the vinylether "Intermediate-A" (MS: (Turbo Spray) 277 (33%), 275 (M+H$^+$, 100%), 231 (22%), 229 (84%), 205 (11%)). After cooling to 50° C., 25% HCl (15 equiv) was added. The mixture was kept at this temperature for 1 h. After workup, the azaindole 8 was isolated as a crystalline solid in 92% yield. MS (Turbo Spray): 231 (26%), 229 (M+H$^+$, 100%).

I-b) Cyclization of the Bromide:

To a mixture of bromide (5b) and pinacol vinylboronate (6, 1.2 equiv) in DMF was added LiOH (3 equiv) followed by PdCl$_2$(dppf).CH$_2$Cl$_2$ (3 mol %). The reaction mixture was heated to 70° C. and stirred for 18 h. HPLC analysis indicated complete conversion to the vinylether intermediate. After cooling the reaction mixture to 50° C., HCl (25%) was added and the mixture was stirred at this temperature for 1 h. The reaction was complete at this point. After workup, compound 8 was isolated as a crystalline solid in 78% yield. MS (Turbo Spray): 231 (35%), 229 (M+H$^+$, 100%).

II. Catechol Vinylboronate Coupling

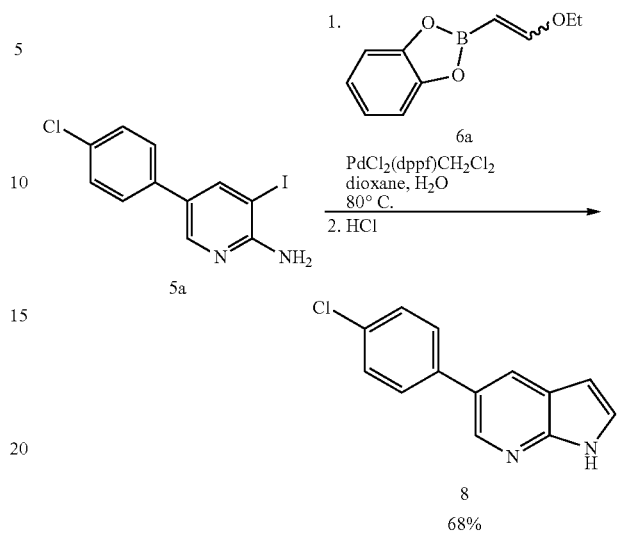

To a mixture of iodide (5a) and catechol vinylboronate (6a, 1.1 equiv) in dioxane/water (80:20) was added LiOH (3 equiv) followed by PdCl$_2$(dppf).CH$_2$Cl$_2$ (3 mol %). The reaction mixture was heated to 80° C. and stirred for 24 h. HPLC analysis indicated complete conversion to the vinylether intermediate. After cooling to 50° C., 25% HCl (15 equiv) was added and the mixture was kept at this temperature for 1 h. After workup, the azaindole 8 was isolated as a crystalline solid in 68% yield. MS (Turbo Spray): 231 (26%), 229 (M+H$^+$, 100%)

Example 4

Propane-1-sulfonic acid {3-[5-(4-chloro-phenyl)-1H-pyrrolo[2,3-b]pyridine-3-carbonyl]-2,4-difluoro-phenyl}-amide (1)

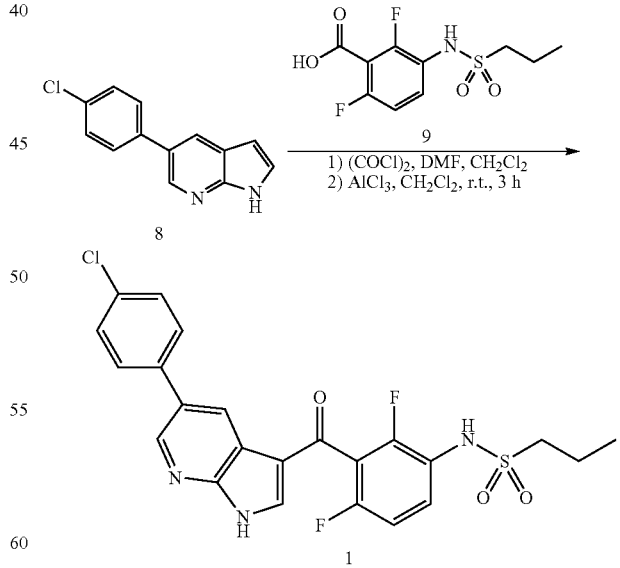

A suspension of sulfonamide acid (9) (1.2 eq.) in CH$_2$Cl$_2$ was treated at room temperature with cat. amount of DMF (0.11 eq.). Within 30 min a solution of oxalylchloride (1.30 eq.) in CH$_2$Cl$_2$ was added and the reaction mixture was stirred for 2 h, whereby the corresponding acid chloride was formed.

A suspension of aluminium chloride (AlCl₃, 4 eq.) in CH₂Cl₂ was treated at 0° C. with a solution of Cl-phenyl azaindole (8) in CH₂Cl₂. To the reaction mixture was subsequently added at room temperature the freshly prepared (above described) acid chloride. Stirring at room temperature for 3 h, aqueous work-up and crystallization from THF/heptane provided the title compound (1) as off-white powder in 85% yield. MS (Turbo Spry): 509 (48%), 507 (M+NH₄⁺, 100%), 492 (40%), 490 (M+H⁺, 84%).

Example 5

5-(4-Cl-phenyl)azaindole (8, via Sonogashira reaction)

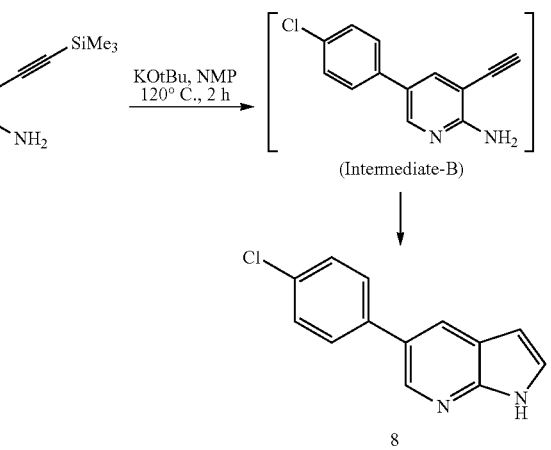

A solution of bromide 5b in toluene was degassed with argon and then treated with PdCl₂(PPh₃)₂Cl₂ (0.17 eq.) and CuI (0.17 eq.) and degassed with argon again. To the suspension was added tetramethylguanidine (1.4 eq.) and ethyltrimethylsilane (2 eq.) and stirred at 100° C. for 2 h. After cooling to room temperature, extractive work-up and chromatographic purification the intermediate F was collected in 93% yield. MS (Turbo Spray): 303 (49%), 301 (M+H⁺, 100%)

A solution of the intermediate F in 1-methyl-2-pyrrolidinone (NMP) was treated at room temperature with potassium tert. butylate (2 eq.). The mixture was heated to 120° C. and stirred for 2 h. After cooling to room temperature, extractive work-up and crystallization from EtOH/water the title compound (8) was collected in 80% yield. MS (Turbo Spray): 231 (26%), 229 (M+H⁺, 100%)

Intermediate X: MS (Turbo Spray): 231 (41%), 229 (M+H⁺, 100%)

Example 6

2-amino-5-bromo-3-iodopyridine (11)

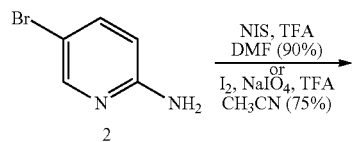

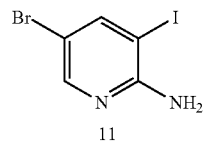

a) NIS Procedure:

To a solution of 2-amino-5-bromopyridine (2) in DMF was added trifluoroacetic acid (1.2 equiv). At room temperature, N-iodosuccinimide (1.1 equiv) was added and the reaction mixture was heated at 50° C. for 3 h. HPLC indicated complete conversion. After cooling to room temperature the product was precipitated by adding the reaction mixture to water.

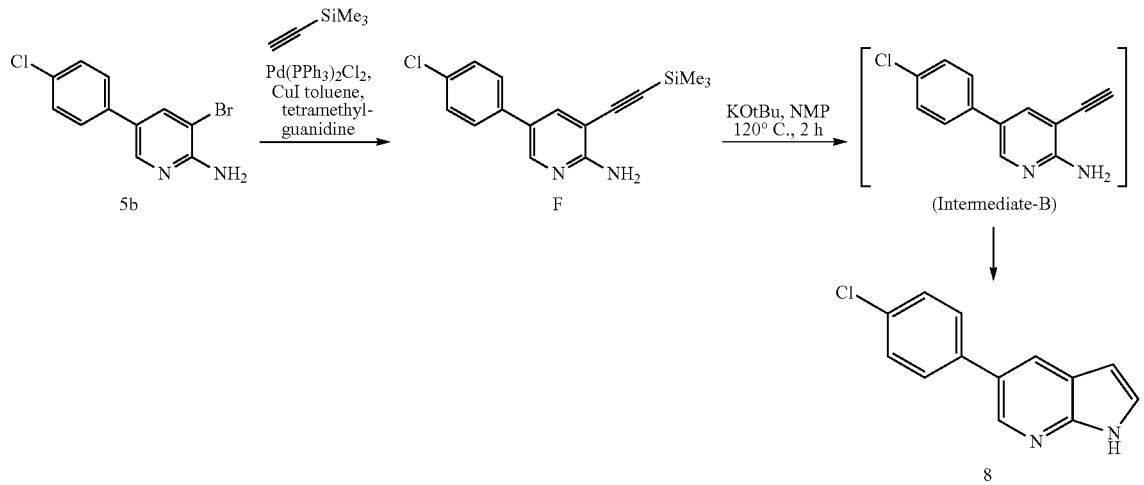

After neutralization with sodiumthiosulfate and 1N NaOH the title compound (11) was collected by filtration as a brown solid in 90% yield.

b) I₂/NaIO₄ Procedure:

To a solution of 2-amino-5-bromopyridine (2) in acetonitrile was added sodiumperiodate (0.4 equiv) and iodine (0.65 equiv). Trifluoroacetic acid (0.65 equiv) was added over 15 min and the reaction mixture was heated at 80° C. overnight. HPLC indicated 96% conversion at this point. An aqueous solution of sodium sulfite was added, followed by more water to precipitate the product which was filtered off and washed with water. The title compound (11) was isolated as a brown crystalline solid in 75% yield. MS (Turbo Spray): 298 (M+H⁺, 100%)

Example 7

5-bromo-7-azaindole (12, via Suzuki-Miyaura reaction)

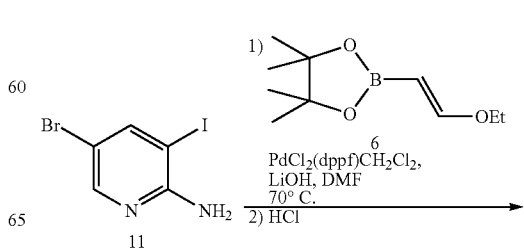

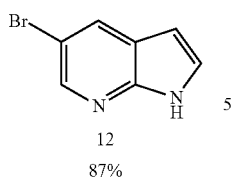

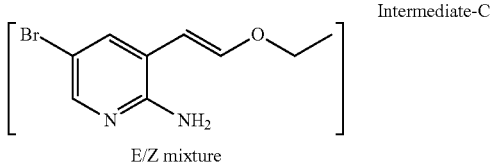

2-Amino-3-iodo-5-bromopyridine (11) was reacted with pinacol vinylethylether boronate (6, 1.3 equiv) in the presence of LiOH (3 equiv) and PdCl$_2$(dppf).CH$_2$Cl$_2$ (1 mol %). After 18 h at 70° C., complete conversion to the amino pyridine vinyl ether was observed (Intermediate-C). The vinyl ether was immediately hydrolyzed by adding 25% HCl and stirring the reaction mixture at 50° C. for 1 h. Workup and crystallization from toluene/heptane gave the title compound (12) in 87% yield. MS (Turbo Spray): 199 (M+H$^+$, 100%). Intermediate: MS (Turbo Spray): 243 (M+H$^+$), 199.

Example 8

5-bromo-7-azaindole (12, via Sonogashira reaction)

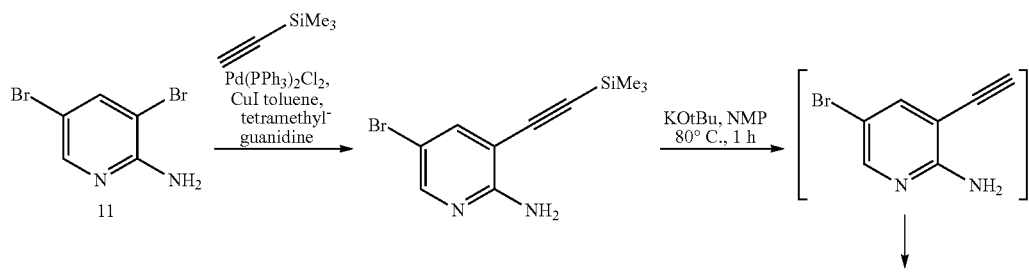

A solution of 2-Amino-3-iodo-5-bromopyridine (11) in toluene was degassed with argon and then treated with PdCl$_2$(PPh$_3$)$_2$Cl$_2$ (0.17 eq.) and CuI (0.17 eq.) and degassed with argon again. To the suspension was added tetramethylguanidine (1.4 eq.) and ethyltrimethylsilane (2 eq.) and stirred at 80° C. for 1 h. After cooling to room temperature, extractive work-up the intermediate was collected in 83% yield as brown solid.

A solution of the intermediate in 1-methyl-2-pyrrolidinone (NMP) was treated at room temperature with potassium tert. butylate (2 eq.). The mixture was heated to 80° C. and stirred for 1 h. After cooling to room temperature, extractive work-up and chromatographic purification the title compound (12) was collected in non optimized 53% yield.

Example 9

Pinacol vinylboronate (6)

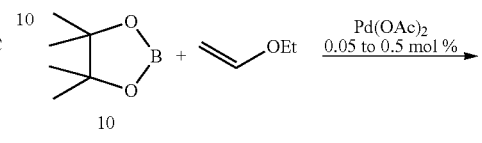

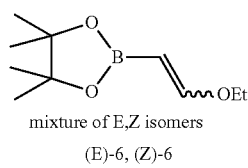

Pinacolborane (10) and 4.1 equivalents of ethyl vinylether are stirred at room temperature in the presence of 0.05 mol % Pd(OAc)$_2$ until reaction completion (20 h). The mixture is then concentrated and the product distilled under vacuum to afford pinacol vinylboronate (6) as a colorless liquid in 83% yield. The product consists of a mixture of E/Z isomers (ratio ca. 2:1). MS (Turbo Spray): 199 (M+H$^+$, 100%), 216 (M+NH$_4^+$).

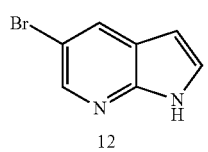

The invention claimed is:
1. A process for the manufacture of a compound of formula A

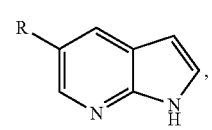

said process being characterized in that a) a compound of formula B

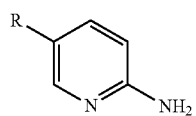
(B)

is reacted in the presence of a halogenation reagent, optionally followed by the introduction of amino-protecting groups, to give a compound of formula C

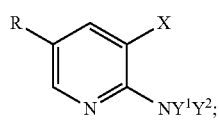
(C)

b) said compound of formula C is further reacted in the presence of a palladium catalyst, a base and a compound of the formula D

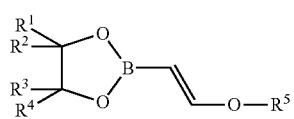
(D)

to give the compound of formula E

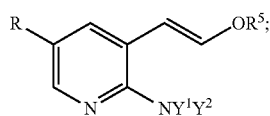
(E)

and c) the compound of formula E is further treated with an acid to give the compound of formula A;

wherein R is phenyl, which is unsubstituted or once or several times substituted by halogen;

$R^1$, $R^2$, $R^3$ and $R^4$ are all methyl, or together with the carbon atoms to which they are attached form a phenyl ring;

$R^5$ is —(C1-C6)alkyl or benzyl;

X is —Br or —I; and $Y^1$ and $Y^2$ are independently selected from the group consisting of benzyl, trifluoroacetyl, acetyl, and hydrogen.

2. The process according to claim 1 for the manufacture of the compound of formula A

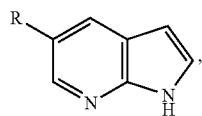
(A)

said process being characterized in that a) a compound of formula B

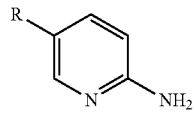
(B)

is reacted in the presence of N-bromosuccinimide (NBS) or N-iodosuccinimide (NIS) or sodium periodate in combination with iodine ($I_2$/$NaIO_4$), optionally followed by the introduction of amino-protecting groups, to give a compound of formula C

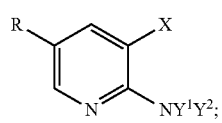
(C)

b) said compound of formula C is further reacted in the presence of $PdCl_2$(dppf)$CH_2Cl_2$, LiOH, and the compound of the formula D

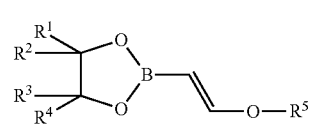
(D)

to give the compound of formula E

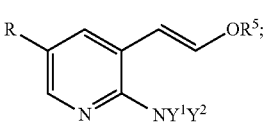
(E)

and c) the compound of formula E is further treated with an acid to give a compound of formula A;

wherein R is phenyl, which is unsubstituted or once or several times substituted by halogen;

$R^1$, $R^2$, $R^3$ and $R^4$ are all methyl, or together with the carbon atoms to which they are attached form a phenyl ring;

$R^5$ is —(C1-C6)alkyl or benzyl;

X is —Br or —I; and $Y^1$ and $Y^2$ are independently selected from the group consisting of benzyl, trifluoroacetyl, acetyl, and hydrogen.

3. The process according to claim 2, wherein

R is 4-Cl-phenyl;

$R^1$ to $R^4$ are all methyl;

$R^5$ is ethyl;

X is —Br; and $Y^1$ and $Y^2$ are both hydrogen.

4. A compound of formula E

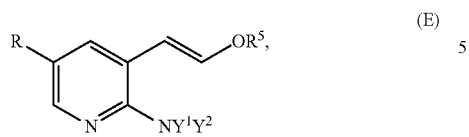
(E)

wherein
R is phenyl, which is unsubstituted or once or several times substituted by halogen;
$R^5$ is —(C1-C6)alkyl or benzyl; and
$Y^1$ and $Y^2$ are each independently selected from the group consisting of benzyl, trifluoroacetyl, acetyl, and hydrogen.

5. The compound of claim 4, wherein R is 4-chlorophenyl, $R^5$ is —(C1-C6)alkyl, and $Y^1$ and $Y^2$ are each hydrogen.

6. The compound of claim 4, which is

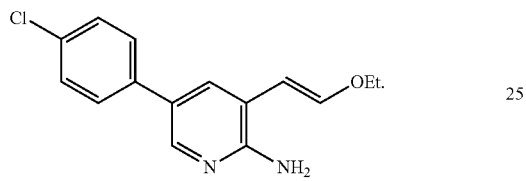

* * * * *

UNITED STATES PATENT AND TRADEMARK OFFICE
CERTIFICATE OF CORRECTION

PATENT NO. : 8,779,150 B2  
APPLICATION NO. : 13/183694  
DATED : July 15, 2014  
INVENTOR(S) : Corey James Brumsted et al.

Page 1 of 1

It is certified that error appears in the above-identified patent and that said Letters Patent is hereby corrected as shown below:

In the Claims

Claim 1, column 25, line 25, change "the formula D" to --formula D--

Claim 1, column 25, line 35, change "the compound of formula E" to --a compound of formula E--

Claim 2, column 26, line 2, change "a compound of formula B" to --the compound of formula B--

Claim 2, column 26, line 16, change "a compound of formula C" to --the compound of formula C--

Claim 2, column 26, line 28, change "the formula D" to --formula D--

Claim 2, column 26, line 50, change "a compound of formula A" to --the compound of formula A--

Signed and Sealed this  
Eleventh Day of August, 2015

Michelle K. Lee  
*Director of the United States Patent and Trademark Office*